(12) United States Patent
Neeman et al.

(10) Patent No.: US 7,867,245 B2
(45) Date of Patent: Jan. 11, 2011

(54) VENOUS FILTERS

(75) Inventors: Ziv Neeman, Merion-Station, PA (US); Bradford J. Wood, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 286 days.

(21) Appl. No.: 10/588,863

(22) PCT Filed: Feb. 8, 2005

(86) PCT No.: PCT/US2005/004076

§ 371 (c)(1), (2), (4) Date: Oct. 23, 2007

(87) PCT Pub. No.: WO2005/077303

PCT Pub. Date: Aug. 25, 2005

(65) Prior Publication Data

US 2008/0234721 A1    Sep. 25, 2008

Related U.S. Application Data

(60) Provisional application No. 60/543,766, filed on Feb. 9, 2004.

(51) Int. Cl.
*A61M 29/00* (2006.01)
(52) U.S. Cl. ..................................... 606/200; 623/1.19
(58) Field of Classification Search .................. 606/200; 623/1.15, 1.19
See application file for complete search history.

(56) References Cited

U.S. PATENT DOCUMENTS

| | | | | |
|---|---|---|---|---|
| 6,007,558 A | * | 12/1999 | Ravenscroft et al. | ........ 606/200 |
| 6,267,776 B1 | * | 7/2001 | O'Connell | ................... 606/200 |
| 6,342,063 B1 | | 1/2002 | Devries et al. | |

(Continued)

OTHER PUBLICATIONS

Ferris et al., "Percutaneous Inferior Vena Caval Filters: Follow-up of Seven Designs in 320 Patients," *Radiology*, vol. 188, pp. 851-856 (Sep. 1993).

(Continued)

*Primary Examiner*—Eduardo C Robert
*Assistant Examiner*—Michael G Mendoza
(74) *Attorney, Agent, or Firm*—Klarquist Sparkman, LLP

(57) ABSTRACT

Venous filters having at least two struts (110) each having a connected end and a non-connected end, wherein each of the struts includes a strut portion and an anchor portion (116), and wherein the strut portion and the anchor portion are attached via an electrolytically active thread (221, 222); and a head (118) that connects the connected ends of the struts, wherein the strut portion can be separated from the anchor portion at least in part by the application of an electrical current. The invention also includes a venous filter having at least two struts, wherein each of the struts includes a temperature sensitive portion and an anchor portion; wherein the anchor portion is separated from the temperature sensitive portion at least in part by changing the temperature around at least the temperature sensitive portion. Also included is a venous filter having a web (650) of dissolvable material; and at least two anchors (618), wherein the at least two anchors are configured to retain the web within a mammalian blood vessel.

18 Claims, 7 Drawing Sheets

U.S. PATENT DOCUMENTS

| | | | |
|---|---|---|---|
| 6,391,044 B1 * | 5/2002 | Yadav et al. | 606/200 |
| 6,972,025 B2 * | 12/2005 | WasDyke | 606/200 |
| 2003/0208227 A1 | 11/2003 | Thomas | |
| 2004/0158274 A1 | 8/2004 | Wasdyke | |

OTHER PUBLICATIONS

International Search Report dated Sep. 1, 2005, for PCT Application No. PCT/US2005/004076 (published as WO 2005/077303).

Linsenmaier et al., "Indications, Management, and Complications of Temporary Inferior Vena Cava Filters," *Cardiovasc Intervent Radiol*, vol. 21, pp. 464-469 (Oct. 1998).

Neuerburg et al., "Percutaneous Retrieval of the Tulip Vena Cava Filter: Feasibility, Short- and Long-Term Changes—An Experimental Study in Dogs," *Cardiovasc Intervent Radiol*, vol. 24, pp. 418-423 (Dec. 2001).

Schleich et al., "Long-term Follow-up of Percutaneous Vena Cava Filters: a Prospective Study in 100 Consecutive Patients," *Eur. J. Vasc. Endovasc. Surg.*, vol. 21, pp. 450-457 (May 2001).

Written Opinion dated Sep. 1, 2005, for PCT Application No. PCT/US2005/004076 (published as WO 2005/077303).

* cited by examiner

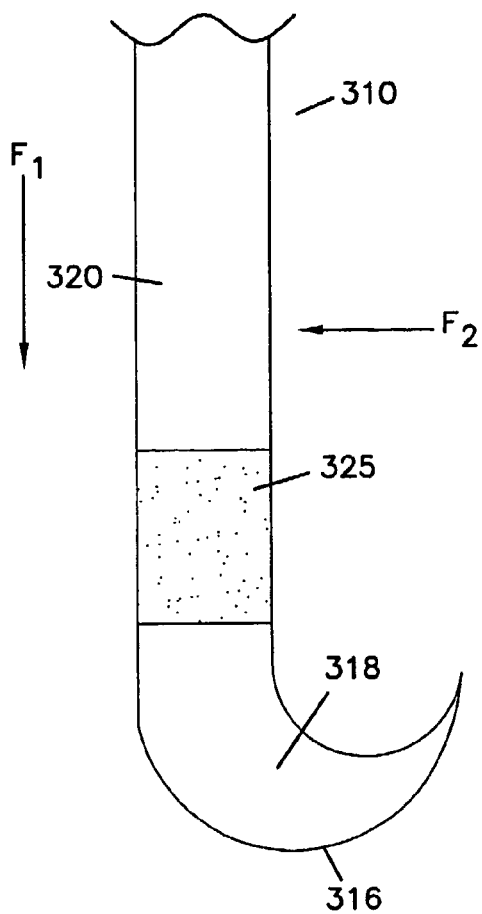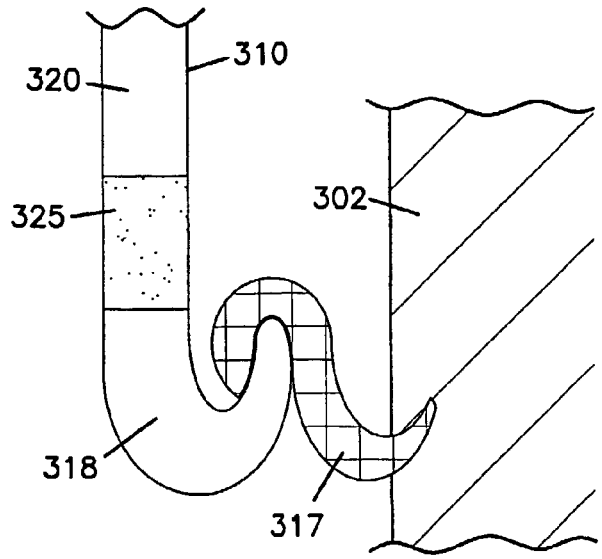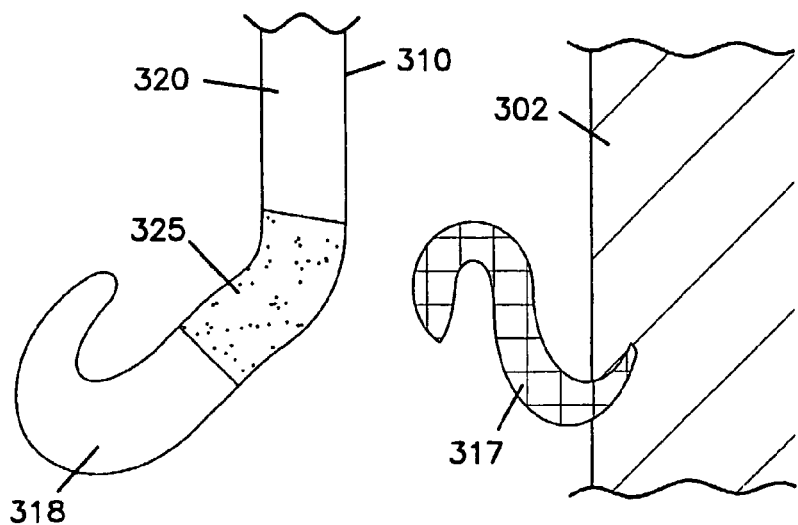

VENOUS FILTERS

This invention is supported by the Department of Health and Human Services. The Government of the United States of America may have certain rights in the invention disclosed and claimed herein below.

This application is a National Stage Application of PCT/US2005/004076, filed 8 Feb. 2005, which is the International Application of Ser. No. 60/543,766, filed 9 Feb. 2004 and which application(s) are incorporated herein by reference. A claim of priority to both, to the extent appropriate is made.

FIELD OF THE INVENTION

The invention includes filters to remove clots from blood that are for use in mammalian veins. More particularly, the invention includes venous filters that are removable.

BACKGROUND OF THE INVENTION

Inferior vena cava (IVC) filters are devices that block the passage of venous emboli from the lower extremities or pelvis through the IVC into the pulmonary arteries. Generally, IVC filters are used to capture potentially fatal pulmonary emboli at an anatomical location where they may pose a minimal risk for the patient. Since the vast majority of pulmonary emboli originate from the lower body parts, filters are mainly placed into the IVC, and only very rarely is there an indication for filter placement in the superior vena cava (SVC).

Numerous filters are available for percutaneous placement in a patient. However, most filters are generally retrievable only up to about 14 days from deployment, because of fibrotic wall reactions and endothelialization that starts on the third week following deployment. Filters that remain longer than 2 weeks generally demonstrate an intimal coverage of the struts that were in contact with the vessel wall. Therefore, any manipulation of these implanted struts after the second week may result in grave injury of the vessel wall with subsequent complications including: life threatening bleeding, dissection of vessel and thrombosis. For this reason, venous filters are generally not used if not absolutely necessary.

A recent publication has demonstrated retrievability up to 134 days (Asch, Radiology Vol. 225 (no. 3), pp. 835-844, December 2002). That study used a recovery nitinol filter (RNF) (NMT Medical, Boston, Mass.), which is composed of 12 0.13 inch nitinol wires that extend from a nitinol sleeve. The filter was removed using a retrieval cone that docked with the filter tip. One possible disadvantage of the filter utilized in Asch is that the anchors must be pulled from the wall and this always creates the possibility of damaging the vessel wall.

Lifetime filters can be utilized in instances where the filter is necessary, but the complications of temporary filters are unacceptable. However, lifetime filters also have risks and complications, including: migration of the filter to the heart or lung, fracture of the filter legs, penetration of the IVC by filter components, thrombosis of the vena-cava, and an increased incidence of lower extremity deep vein thrombosis. Such long term indwelling filters are also associated with a high rate of vena cava clot or venous insufficiency symptoms from the inability of the blood to return to the heart in a hemodynamically efficient manner. In such instances, collateral veins develop, but can generally not handle the high flows around an occlusive vena cava clot surrounding a chronic filter. This can result in massive swelling of the lower extremities, pain and markedly dilated lower extremity veins. Such symptoms may occur for the lifetime of the patient and may be debilitating.

Because of the problems of removing temporary IVC filters, and the side effects of lifetime filters, there remains a need for a temporary filter that can be removed with a decreased amount or severity of complications.

SUMMARY OF THE INVENTION

One embodiment of the invention includes a venous filter having at least two struts each having a connected end and a non-connected end, wherein each of the struts includes a strut portion and an anchor portion, and wherein the strut portion and the anchor portion are attached via an electrolytically active thread; and a head that connects the connected ends of the struts, wherein the strut portion can be separated from the anchor portion at least in part by the application of an electrical current.

Another embodiment of the invention includes a venous filter having at least two struts, each having a connected and a non-connected end, wherein each of the struts includes a temperature sensitive portion and an anchor portion; a head that connects the connected ends of the struts, wherein the anchor portion is separated from the temperature sensitive portion at least in part by changing the temperature around at least the temperature sensitive portion.

A further embodiment of the invention includes a venous filter having a web of dissolvable material; and at least two anchors, wherein the at least two anchors are configured to retain the web within a mammalian blood vessel.

BRIEF DESCRIPTION OF THE FIGURES

FIG. 3A is a longitudinal cross section of a portion of a strut of a filter in accordance with the invention.

FIG. 3B is s longitudinal cross section of a portion of a strut of a filter and hook imbedded in a blood vessel wall, in accordance with the invention.

FIG. 3C is the embodiment of FIG. 3B after at least the temperature sensitive portion has been exposed to a temperature change.

DETAILED DESCRIPTION OF THE INVENTION

Figure 1:
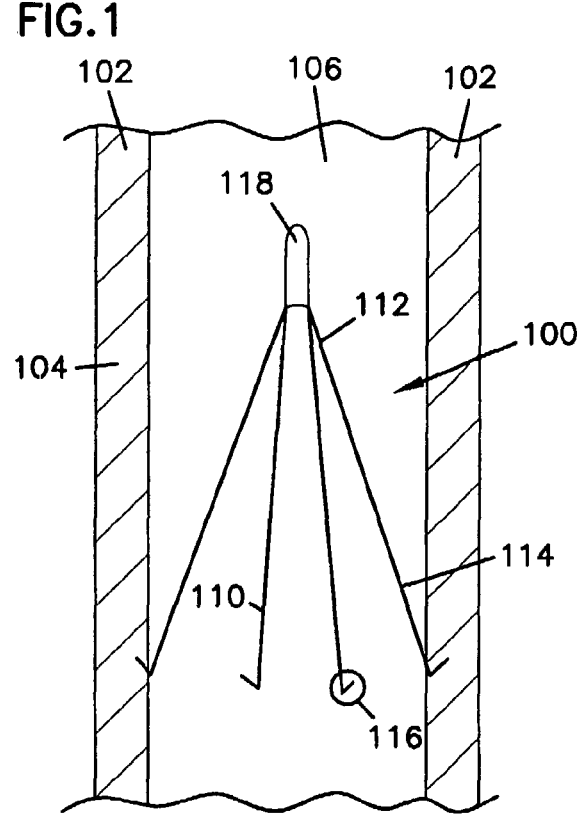
FIG. 1 is a plan view of a venous filter disposed in a blood vessel with the blood vessel shown in longitudinal cross section.

FIG. 1 depicts a venous filter 100 disposed in a blood vessel 104. The blood vessel 104 includes walls 102 that create a lumen 106. The venous filter 100, when deployed, is located within the lumen 106 and is anchored in some fashion within the walls 102.

The venous filter 100 has a generally conical shape. The venous filter 100 includes at least one strut 110 and a head 118. The number of struts 110, and the configuration of the struts 110 may vary depending on the particular type of venous filter 100. Each of the struts 110 has a connected end 112 and a non-connected end 114. The connected ends 114 of the struts 110 are connected by or within the head 118.

At least one of the struts 110 has an anchor 116 on the non-connected end 114. In some venous filters, such as that shown in FIG. 1, each of the struts 110 has an anchor 116 on the non-connected end 114. When deployed in a blood vessel 104, the non-connected ends 114 contact the wall 102. The anchors 116 then contact the wall 102 so that the anchors 116 can become imbedded in the wall 102.

When it is desired to remove the venous filter 100 from the blood vessel 104, it becomes necessary when using some prior art venous filters to remove the anchors 116 from the wall 102. Many prior art venous filters, such as that depicted in FIG. 1, can cause significant damage to the wall 102 when the anchors 116 are removed from the wall 102.

The venous filters of the invention are configured so that the removal thereof from the blood vessel does not cause significant or life threatening damage to the vessel wall, or are alternatively configured so that they do not have to be removed from the vessel wall. The venous filters of the invention accomplish this either through use of improved mechanical methods for dislodgement that leave the anchors behind, such as, electrolytically active threads between the struts and the anchors, weakened areas that allow easy removal or through use of dissolvable filters that don't need to be removed, but simply dissolve in place.

Mechanical Mechanisms for Dislodgement

Venous filters of the invention that utilize improved mechanical mechanisms for dislodgment include the use of electrolytically active threads between the struts and the anchors, and weakened areas that allow easy removal.

Figure 2A:
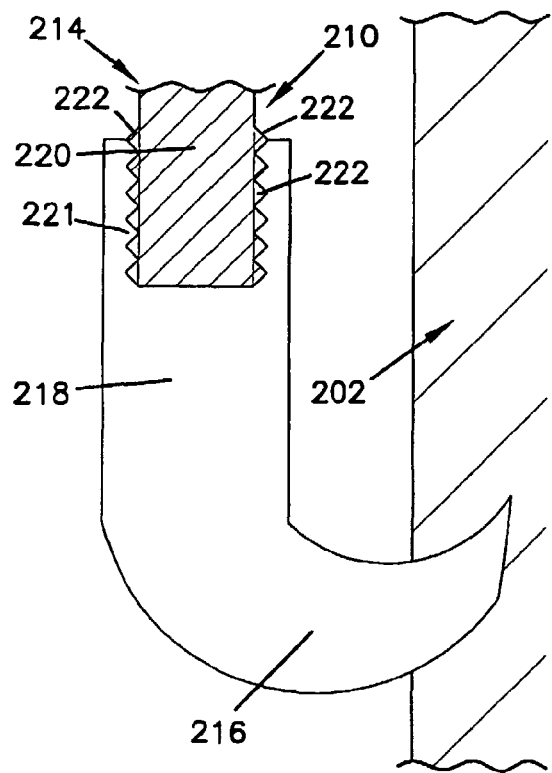
FIG. 2A is a longitudinal cross section of a portion of a strut of a filter in accordance with the invention imbedded in a blood vessel wall.

An enlarged view of one of the struts of a venous filter in accordance with an embodiment of the invention is depicted in FIG. 2. The strut 210 depicted in FIG. 2 includes an anchor 216 on the proximal end 214 thereof. In this embodiment of the invention, the strut 210 includes two separate pieces, a strut portion 220 and an anchor portion 218. The anchor portion 218 is configured with corresponding negative threads 221 that attach the anchor portion 218 to the strut portion 220 via the positive threads 222. In the embodiment depicted in FIG. 2, the strut portion 220 is configured with the positive threads 222, and the anchor portion 216 is configured to receive those positive threads 222 with negative threads 221. Alternatively, one of skill in the art, having read this specification, would understand that the anchor portion 218 could be configured with the positive threads 222 and the strut portion could be configured to receive those positive threads by having negative threads 221.

The positive threads 222, the negative threads 221, or both are made of a material that is electrolytically active. As used herein, electrolytically active means that the material can be eroded or at least mostly dissolved by application of an electrical current. Generally, it is desirable but not required that the material be at least mostly dissolved in less than about two minutes. In one embodiment, the electrolytically active material is at least mostly dissolved in less than about one minute. Generally, an electrical current of approximately about 0.01-2 milliamps at about 0.1 to 15 volts is applied to the electrolytically active material in order to dissolve or erode it.

Examples of electrolytically active material that could be used for the threads 222 include metals and alloys of the platinum group, such as for example, platinum, rhodium, palladium, and rhenium, tungsten, gold, silver, tantalum, and alloys thereof. Stainless steel and "super-elastic alloys" including nickel/titanium alloys (48-58 atomic % nickel and optionally containing modest amounts of iron), copper/zinc alloys (38-42 weight % zinc), copper/zinc alloys containing 1-10 weight % benzillium, silicon, tin, aluminum or gallium, and nickel/aluminum alloys (36-38 atomic % aluminum).

One of skill in the art, having read this specification would understand that the positive threads 222 and the negative threads could be manufactured by any number of means. In one embodiment the entire strut 210 can be made out of the electrolytically active material and all of its surface, except the region of the positive and/or negative threads, can be covered by an insulating material. The industry material can be any non-conducting, biocompatible material known to those of skill in the art, having read this specification. Examples of insulating materials include, but are not limited to, polymers such as polytetrafluoroethylene (Teflon®), polyurethanes, polyethylenes, polypropylenes, polyethylene terephthalates, polyvinylchloride, or parylenes.

The size and dimensions of the threads are determined in light of the size of the struts 210 themselves and the function of the thread area. The threads are configured to controllably erode and release the remainder of the filter 100 so that it can be removed from the blood vessel wall. Generally, the threads are of a size that are large enough to meet structural requirements but small enough to erode quickly. As used herein, "erode quickly" means that they can erode or at least mostly dissolve in less than about 2 minutes.

Figure 2B:
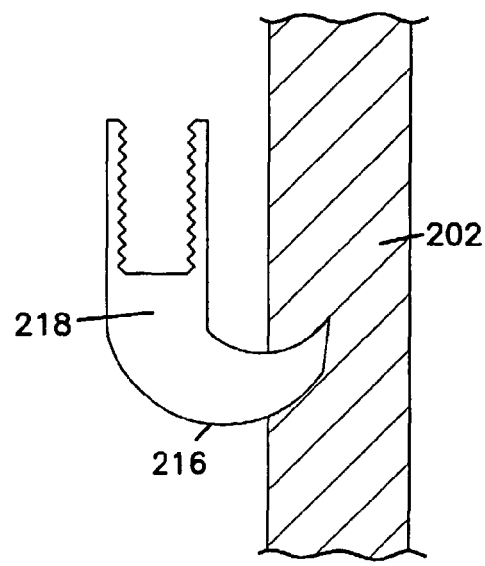
FIG. 2B is a longitudinal cross section of an anchor remaining after the filter of FIG. 2A has been removed from the blood vessel wall.

In this embodiment, the electrolytically active positive threads 222 allow the majority of the venous filter to be removed from the wall 204 of the blood vessel with minimal damage to the wall 202 by applying an electric current to the exposed threads 222. Application of an electric current would cause the threads 222 to erode, which would then allow the strut portion 220 to be removed from the anchor portion 218. This would accomplish the removal of the filter without damage to the wall 202 because the anchor portion 218, which is imbedded in the wall 202, would not be dislodged from the wall 202. The blood vessel wall 202, after removal of the strut portion 220 from the filter is shown in FIG. 2B.

An enlarged view of a venous filter in accordance with another embodiment of the invention is depicted in FIG. 3. The strut 310 depicted in FIG. 3 includes a strut portion 320, an anchor portion 318, and a temperature sensitive portion 325. The strut portion 320 can be made of any material, known to one of skill in the art, having read this specification, as being useful for struts in venous filters. In one embodiment, the struts are made of either stainless steel or nitinol. The anchor portion 318 can also be made of any material, known to one of skill in the art, having read this specification, as being useful for the anchors of venous filters. Generally, the anchors can be made of the same material as the struts. In one embodiment, the anchors are made either of stainless steel or nitinol. In another embodiment, the anchors are not made of the same material as the struts are.

The temperature sensitive portion 325 is made of a material whose tensile strength changes in response to a temperature change. Examples of materials that can be utilized for the temperature sensitive portion 325 include shape memory alloys. Specific examples of shape memory alloys include nickel-titanium alloys, and copper alloys such as CuZnAl and CuAlNi. An exemplary nickel-titanium alloy is generally known in the art as Nitinol. Nitinol is commercially available from TiNi Alloy Company (San Leandro, Calif.), Memory Technologies (Brookfield, Conn.), and Shape Memory Applications (Sunnyvale, Calif.).

Generally the material that is utilized to make the temperature sensitive portion 325 of the strut 310 is chosen so that the material will be stiff at normal body temperatures, but can be made flexible in lower temperatures. One specific example of a material that could be used for the temperature sensitive portion 325 could be a material that is stiff at normal body temperatures (37° C. or 98.6° F.), but becomes flexible at an average room temperature (25° C. or 77° F.). In another embodiment, the temperature sensitive portion 325 could be made out of a material that becomes flexible at a temperature above body temperature. In one embodiment, the temperature sensitive portion 325 becomes flexible at a temperature of about 400-50° C. It is generally not desirable to have the temperature sensitive portion 325 become flexible at a temperature greater than about 50° C. because clotting can occur at this temperature.

A venous filter in accordance with this embodiment of the invention can be removed by changing the temperature around at least the temperature sensitive portion 325 of the strut 310. One method of affecting the temperature around at least the temperature sensitive portion 325 of the strut 310 includes infusing cool saline solution into the area around the venous filter. This could be accomplished, for example, using a sheath that goes around the venous filter. Other methods known to one of skill in the art, having read this specification, that could decrease the temperature in the area at least around the temperature sensitive portion 325 of the strut 310 could also be utilized.

Once the temperature around at least the temperature sensitive portion 325 of the strut 310 is lowered, the temperature sensitive portion 325 will either fracture, or be more easily induced to fracture. One method of inducing the temperature sensitive portion 325 to fracture could include the application of force to the filter. For example, force could be applied in a direction substantially parallel to the longitudinal axis of the strut 310 and towards the anchor portion 316 of the strut 310, as is depicted by the arrow $F_1$ in FIG. 3A. Alternatively, a force could be applied in a direction substantially perpendicular to the longitudinal axis of the strut 310, and away from the blood vessel wall, as is depicted by the arrow $F_2$ in FIG. 3A. Such a force could be applied by placing a sheath over the entirety of the filter so that the struts of the filter are forced in towards the axis of the head of the filter.

Alternatively, the filter containing the temperature sensitive portion 325 could be "hooked" to a hook 317 that is imbedded in the blood vessel wall. An example of such an embodiment is seen in FIG. 3B. FIG. 3C depicts a possible configuration of the temperature sensitive portion 325 after the temperature has been decreased around at least the temperature sensitive portion 325. As seen there, the temperature sensitive portion 325 "unhooks" from the hook 317 causing the venous filter to be removed from the blood vessel without dislodging the hook 317 from the wall. It will also be understood, by one of skill in the art, having read this specification, that the hook 317 could also be made entirely, or partially of a temperature sensitive material.

Figure 4A:
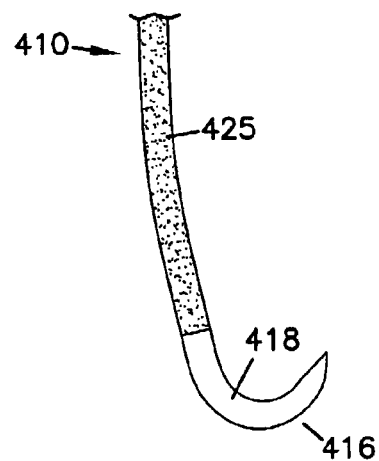
FIGS. 4A and 4B are plan views of a strut of a filter in accordance with the invention before (FIG. 4A) and after (FIG. 4B) a temperature change.

FIG. 4A depicts another embodiment of the invention that utilizes shape memory alloys. In the embodiment depicted in FIG. 4A, the strut 410 includes a temperature sensitive portion 425 and an anchor portion 418. The anchor portion 418 can be made of any material, known to one of skill in the art, having read this specification, as being useful for the anchors of venous filters. The temperature sensitive portion 425 is made of a material whose tensile strength changes in response to a temperature change. Examples of materials that can be utilized for the temperature sensitive portion 425 include shape memory alloys. Specific examples of shape memory alloys include nickel-titanium alloys, and copper bases alloys such as CuZnAl and CuAlNi. An exemplary nickel-titanium alloy is generally known in the art as Nitinol. Nitinol is commercially available from TiNi Alloy Company (San Leandro, Calif.), Memory Technologies (Brookfield, Conn.), and Shape Memory Applications (Sunnyvale, Calif.).

Generally the material that is utilized to make the temperature sensitive portion 425 of the strut 410 is chosen so that the material will be stiff at normal body temperatures, but can be made flexible in lower temperatures. One specific example of a material that could be used for the temperature sensitive portion 425 could be a material that is stiff at normal body temperatures (37° C. or 98.6° F.), but becomes flexible at an average room temperature (25° C. or 77° F.).

A venous filter in accordance with this embodiment of the invention can be removed by changing the temperature around at least the temperature sensitive portion 425 of the strut 410. One method of affecting the temperature around at least the temperature sensitive portion 425 of the strut 410 includes infusing cool saline solution into the area around the venous filter. This could be accomplished, for example, using a sheath that goes around the venous filter. Other methods known to one of skill in the art, having read this specification, that could decrease the temperature in the area at least around the temperature sensitive portion 425 of the strut 410 could also be utilized.

Figure 4B:
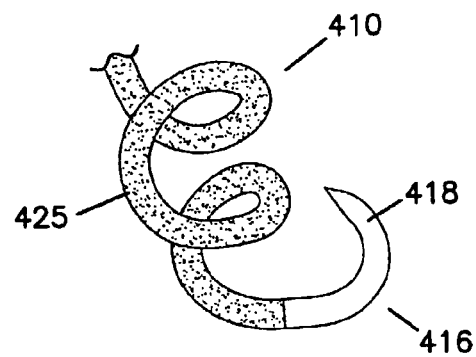

Once the temperature is decreased at least around the temperature sensitive portion 425, the temperature sensitive portion 425 in this embodiment will change from a substantially straight configuration, as seen in FIG. 4A to the coiled configuration in FIG. 4B. Generally, the coiled configuration is easier to break because the coil increases the tension in the temperature sensitive portion 425.

Figure 4C:
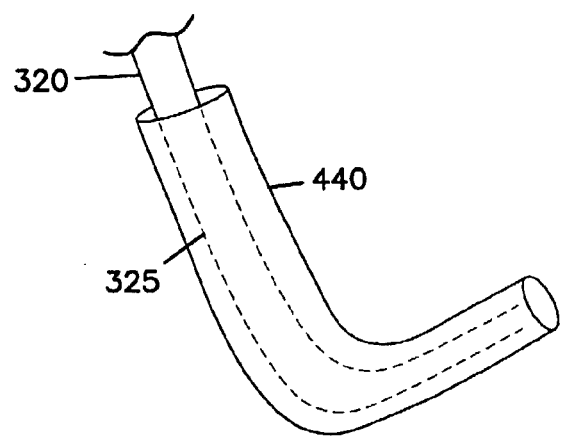
FIGS. 4C, 4D, and 4E are plan views of temperature sensitive portions of a strut of a filter in accordance with the invention.

FIG. 4C depicts another embodiment of the invention that includes both a temperature sensitive portion 325 and a sleeve portion 440. In such an embodiment, when the temperature sensitive portion 325 is exposed to a different temperature, the temperature sensitive portion 325 changes shape, but the sleeve portion 440 does not. This causes the temperature sensitive portion 325 to change shape and straighten, for example, so that it is dislodged from the wall easier than it would have been if still curved. The sleeve portion 440 remains imbedded in the wall once the temperature sensitive portion 325 is dislodged. In one embodiment, the sleeve portion 440 is made of any material that does not change configuration when exposed to a change in temperature. Examples of materials that can be used for sleeve portion 440 include, but are not limited to stainless steel, biodegradable materials, titanium, and certain metal alloys (e.g. cobalt alloys). In one embodiment, this material is stainless steel.

Figure 4D:
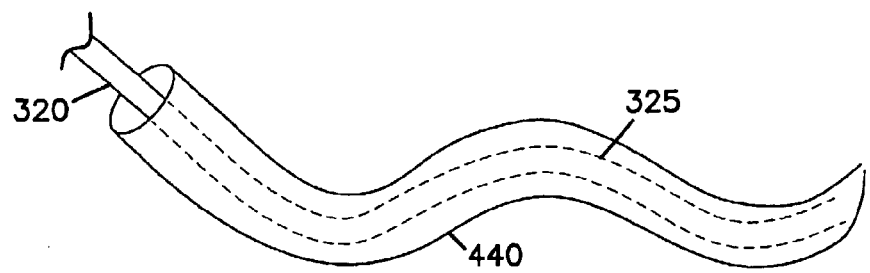

FIG. 4D depicts a further embodiment that utilizes a sleeve portion. The embodiment depicted in FIG. 4D utilizes the same type of mechanism, in that the sleeve portion does not change configuration in a response to a temperature change, but the temperature sensitive portion does. In this embodiment, the temperature sensitive portion 325 and the sleeve portion 440 have at least a slight undulating shape to them. When at least the temperature sensitive portion 325 is exposed to a change in temperature, the temperature sensitive portion 325 changes shape and is released from the sleeve portion 440.

Figure 4E:
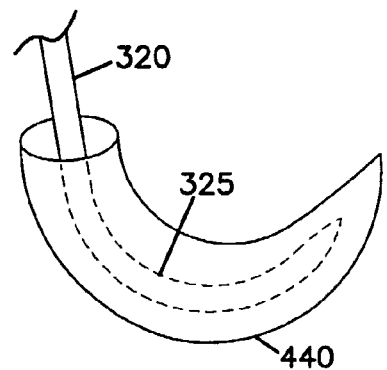

FIG. 4E depicts yet a further embodiment that is similar to the embodiment depicted in FIG. 4C. This embodiment differs in that the portion that is imbedded in the vessel wall is more hook like as opposed to FIG. 4C being more like a right angle. The two embodiments could be used for placement in different vessels, for example.

Figure 4F:
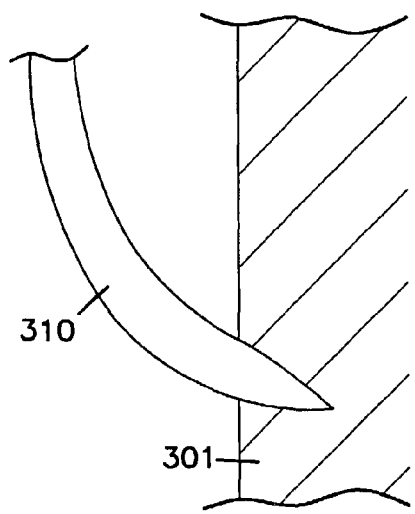
FIGS. 4F and 4G are plan views of another embodiment of the invention that has a strut that is made entirely of nitinol before (FIG. 4F) and after (FIG. 4G) exposure to a temperature change.
Figure 4G:
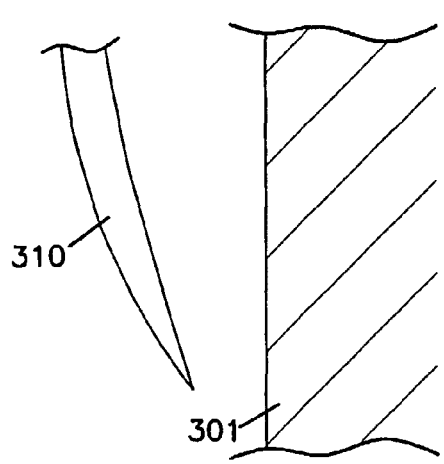

FIG. 4F depicts a further embodiment of the invention where the entire strut 310 is made of a temperature sensitive material. FIG. 4F shows the configuration of such a filter in the blood vessel wall 301, while FIG. 4G shows the configuration of such a filter after the temperature around at least the portion of the strut 310 that is imbedded in the wall is changed.

Figure 5A:
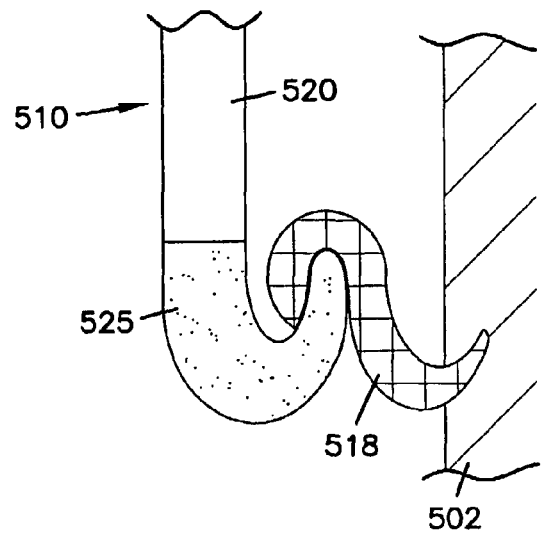
FIGS. 5A and 5B are longitudinal cross sections of a portion of a strut of a filter in accordance with the invention imbedded in a blood vessel wall before (FIG. 5A) and after (FIG. 5B) a temperature change.

Another embodiment of the invention that utilizes a shape memory alloy can be seen in FIG. 5A. The strut 510 in FIG. 5A includes strut portion 520, temperature sensitive portion 525, and anchor portion 518. The strut portion 520, the temperature sensitive portion 525, and the anchor portion 518 can be deployed as one unit, or the anchor portion 518 can be deployed separately from the strut portion 520 and the temperature sensitive portion 525.

The strut portion 520 can be made of any material, known to one of skill in the art, having read this specification, as being useful for the strut portion 520 of the venous filter. Similarly, the anchor portion 518 can be made of any material, known to one of skill in the art, having read this specification, as being useful for the anchor portion 518 of the venous filter.

The temperature sensitive portion 525 is made of a material whose tensile strength changes in response to a temperature change. Examples of materials that can be utilized for the temperature sensitive portion 525 include shape memory alloys. Specific examples of shape memory alloys include nickel-titanium alloys, and copper bases alloys such as CuZnAl and CuAlNi. An exemplary nickel-titanium alloy is generally known in the art as Nitinol. Nitinol is commercially available from TiNi Alloy Company (San Leandro, Calif.), Memory Technologies (Brookfield, Conn.), and Shape Memory Applications (Sunnyvale, Calif.).

Generally the material that is utilized to make the temperature sensitive portion 525 of the strut 510 is chosen so that the material will be stiff at normal body temperatures, but can be made flexible at lower temperatures. One specific example of a material that could be used for the temperature sensitive portion 525 could be a material that is stiff at normal body temperatures (37° C. or 98.6° F.), but becomes flexible at an average room temperature (25° C. or 77° F.).

A venous filter in accordance with this embodiment of the invention can be removed by changing the temperature around at least the temperature sensitive portion 525 of the strut 510. One method of affecting the temperature around at least the temperature sensitive portion 525 of the strut 510 includes infusing cool saline solution into the area around the venous filter. This could be accomplished, for example, using a sheath that goes around the venous filter. Other methods known to one of skill in the art, having read this specification, that could decrease the temperature in the area at least around the temperature sensitive portion 525 of the strut 510 could also be utilized.

Figure 5B:
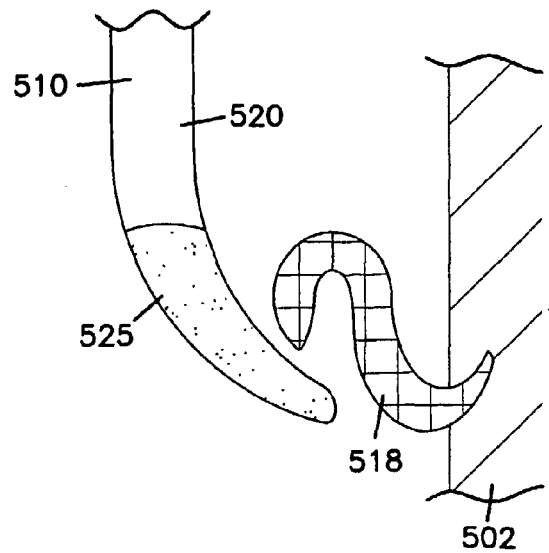

Once the temperature is decreased around at least the temperature sensitive portion 525 of the strut 510, the temperature sensitive portion 525 will change its configuration. FIG. 5B depicts a possible configuration of the temperature sensitive portion 525 after the temperature has been decreased around at least the temperature sensitive portion 525. As seen there, the temperature sensitive portion 525 "unhooks" from the anchor portion 518 causing the venous filter to be removed from the blood vessel without dislodging the anchor portion 518 from the wall.

One of skill in the art, having read this specification, will also understand that the anchor portion 518 could also be made of a shape memory alloy. In an embodiment where the anchor portion 518 is made of a shape memory alloy, the temperature sensitive portion 525 may or may not be made from a shape memory alloy.

One of skill in the art, having read this specification, will also understand that other configurations of the temperature sensitive portion and the anchor portion are also within the scope of this invention. Any configuration that creates a lock and key type system that is "locked" at normal body temperatures and can be "unlocked" by cooling the area can be utilized. Another possible embodiment includes a temperature sensitive portion that has an "M-shaped" configuration at normal body temperatures and becomes straight after the temperature is changes.

Dissolvable Filters

Other venous filters of the invention are dislodged because of the material that they are constructed of. Venous filters in accordance with this embodiment of the invention are deployed into a blood vessel and gradually disappear as the normal bodily fluid that they come in contact with dissolve the material that they are made of. Venous filters of this embodiment are configured, either through the composition of the material or the configuration of the material to begin to dissolve in the center before they begin to dissolve at the periphery. Generally, venous filters in accordance with this embodiment are made of a dissolvable material. In another embodiment, venous filters in accordance with the invention are made of material that is dissolvable, biocompatible, and flexible. The invention also contemplates the use of degradable thermoplastic polymers as the dissolvable materials. An example of a degradable thermoplastic polymer can be found at Lendlein et al., Science, Vol. 293, pp. 1673-1676 (2002).

Examples of dissolvable materials that can be used to make filters in accordance with this embodiment of the invention include, but is not limited to, catgut, treated catgut (mild chromic gut), polyglycolic acid such as SURUCRYL™, polylactic acid such as polyglactin-910 (Vicryl), polydioxanone (PDS), polyglyconate (Maxon), polyglecaprone 25 (Monocryl), pectin, agar, arabic gum, xanthum gum, tragacanth gum, karaya alginic acid or its salt (e.g. sodium alginate), carrageenan, dextrin, starches (such as for example corn starch, rice starch, wheat starch, potato starch, pueraria starch, tapioca starch, carboxymethyl starch, hydroxypropyl starch, hydroxyethyl starch, chemically cross-linked starch, α-starch), celluloses (such as for example hydroxypropylmethyl cellulose, carboxymethyl cellulose, methyl cellulose, methylethyl cellulose, hydroxypropyl cellulose, crystalline cellulose), polyvinyl alcohol, polyvinylpyrrolidone, polyethylene glycol (macrogol), and mannans.

In another embodiment, the dissolvable material utilized in a filter of the invention can include hydrogels, elastin-like peptides, and polyhydroxyalkanoates (PHAs). Examples of these materials can be found in Lee, K. Y. et al Controlling mechanical and swelling properties of alginate hydrogels independently by cross-linker type and cross-linking density; *Macromolecules* 33, 4291-4294 (2000); Temenoff, J. S., Athanasiou, K. A., LeBaron, R. G. & Mikos, A. G, Effect of poly(ethylene glycol) molecular weight on tensile and swelling properties of olio(poly(ethylene glycol) fumarate) hydrogels for cartilage tissue engineering, *J. Biomed. Mater. Res.* 59, 4290437 (2002); van Hest, J. C. M. & Tirrell, D. A., Protein-based materials, toward a new level of structural control, *Chem Comm.*, 19, 1897-1904 (2001); Welsh, E. R. & Tirrell, D. A., Engineering the extracellular matrix: a novel approach to polymeric biomaterials. I. Control of the physical properties of artificial protein matrices designed to support adhesion of vascular endothelial cells, *Biomacromolecules* 1, 23-30 (2000); Urry, D. W. et al., Elastic protein-based polymers in soft tissue augmentation and generation, *J. Biomater. Sci., Polym. Ed.* 9, 1015-1048 (1998); Poirier, Y., Nawrath, C. & Somerville, C., Production of polyhydroxyalkanoates, a family of biodegradable plastics and elastomers, in bacteria and plants, *Biol Technology*, 13, 142-150 (1995); Sodian, R. et al., Fabrication of a trileaflet heart valve scaffold from a polyhydroxyalkanoate biopolyester for use in tissue engineering, *Tissue Eng.*, 6, 183-187 (2000). In yet another embodiment, the material that can be used is a polycondensation polymer of glycerol and sebacic acid. Further information regarding this material can be found in Yadong Wang et al., A tough biodegradable elastomers, *Nature biotechnology*, 20, 606-606 (2002).

Venous filters such as these can have any configuration that is known to those of skill in the art, having read this specification. In one embodiment, the entire venous filter can be made of the dissolvable material. In another embodiment, less than the entire filter is made of dissolvable material. An example of such an embodiment would be one in which the entire filter is made of dissolvable filter, with the exception of the anchor portion of the venous filter.

Venous filters of this embodiment are configured, either through the composition of the material or the configuration of the material to begin to dissolve in the center before they begin to dissolve at the periphery. This can be completed either by physical or chemical means. In one embodiment, this is accomplished by using smaller diameter (or thickness) material at the center of the filter. In another embodiment, this is accomplished by using different, more quickly dissolving material, at the center of the filter. In one further embodiment, this is accomplished by having more material at the periphery than is present at the center.

Figure 6A:
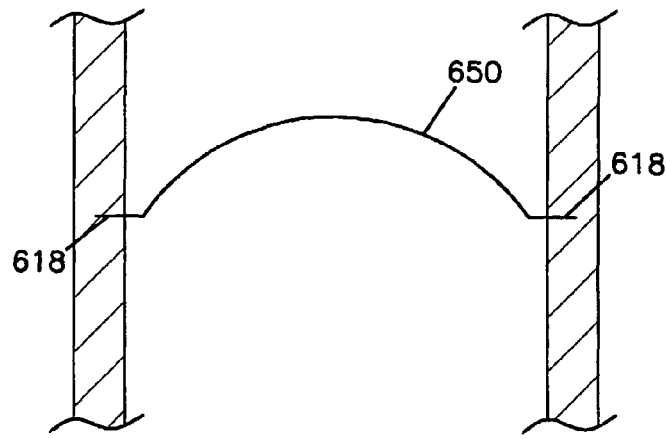
FIGS. 6A, 6B, and 6C are a longitudinal cross section, a plan view, and a longitudinal cross section, respectively of a venous filter in accordance with the invention.
Figure 6B:
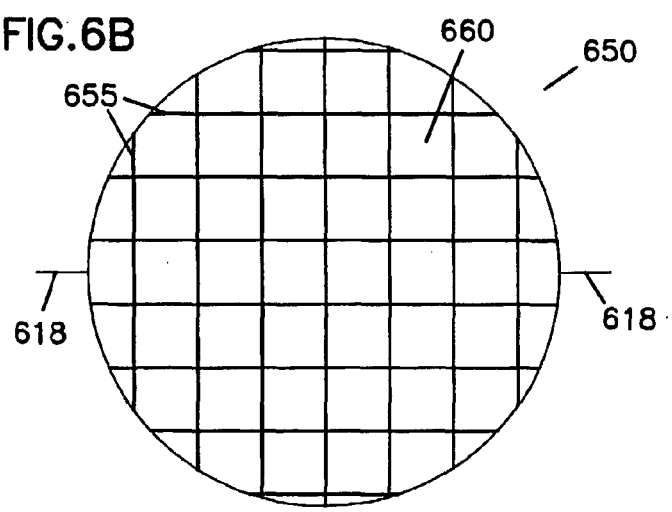

One example of a filter that includes some portion thereof made of a dissolvable material can be seen in FIGS. 6A and 6B. The venous filter in FIG. 6A includes a web 650 that is made at least partially of a dissolvable material and at least two anchors 618. In this embodiment, the web 650 is made of individual fibers 655 of the dissolvable material. In one embodiment, the web 650 has a grid dimension 660 that is not greater than about 10×10 mm. In another embodiment, the web 650, has a grid dimension 660 that is not greater than about 2×5 mm. In yet another embodiment, the web 650 has a grid dimension 660 that is not about 3×5 mm.

Figure 6C:
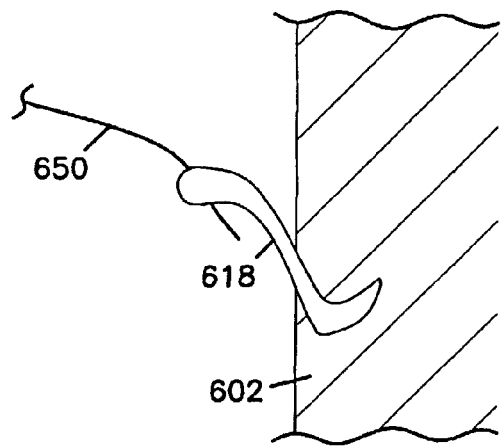

The at least two anchors 618 in this embodiment can be formed of dissolvable material, or non-dissolvable material. However, if the anchors 618 are made of dissolvable material, they should be made of a material that will not dissolve before the web 650 will entirely dissolve. If they are made of non-dissolvable material, they can be made as exemplified in any of the other embodiments included herein. An example of one configuration for anchors 618 is shown in FIG. 6C. As seen there, the anchors 618 are attached to the web 650, and configured to be imbedded into the blood vessel wall 604.

Figure 7:
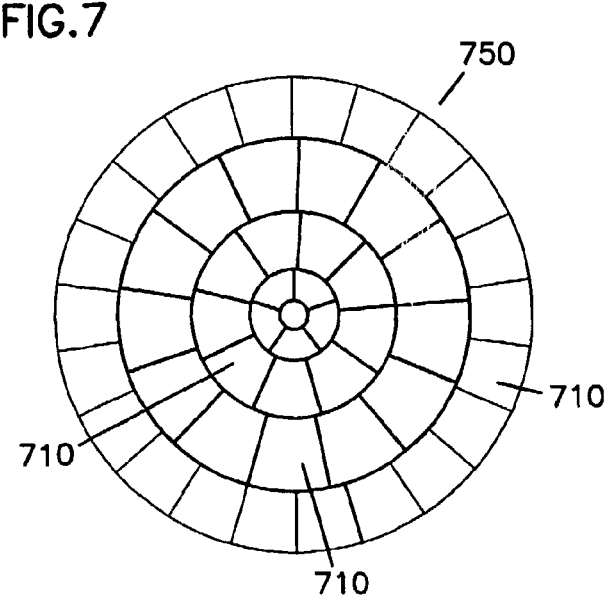
FIG. 7 is a plan view of a venous filter in accordance with the invention.

Another embodiment of a venous filter in accordance with the invention is seen in FIG. 7. In this embodiment, the web 750 is configured from more than one circular piece of dissolvable material. In the embodiment shown in FIG. 7, the web 750 has four concentric circles 710 of dissolvable material. Such an embodiment can be anchored to the vessel wall as previously discussed. In one embodiment, there is no filter or other material in the center of this web.

Figure 8A:
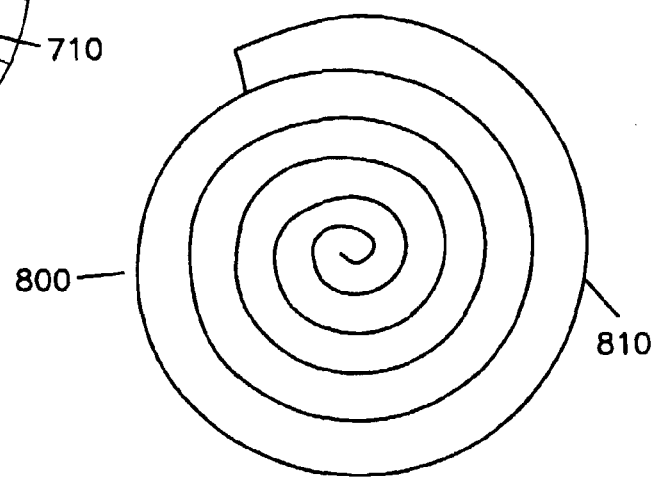
FIGS. 8A and 8B are plan views of venous filters in accordance with the invention.

One alternative embodiment of a dissolvable filter is shown in FIG. 8A and includes a filter 800 that is made of at least one piece of dissolvable material 810 that is spiraled from the outside in. In one embodiment, the one or more pieces of dissolvable material that make up the spiral of the filter has a continual, gradually increasing diameter from the outside to the inside. Such a configuration would cause the filter to dissolve at the inside before it dissolves at the outside, which minimizes the possibility of embolization of the filter. One example of how a portion of the filter could embolize would be for about a 0.5 cm portion of the filter to break off and be release from the filter. This would cause a clot, i.e. the filter and any attached previously caught clots, to be released into the blood flow.

Figure 8B:
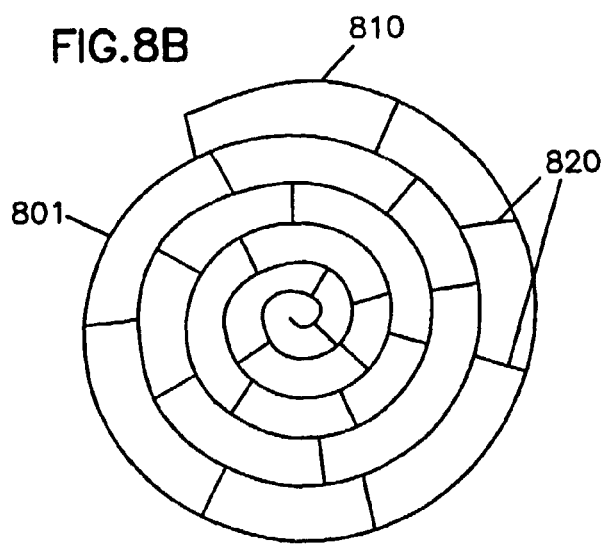

Another embodiment of a dissolvable filter 801 is shown in FIG. 8B and includes a spiraled piece of dissolvable material 810 that is crosslinked with cross pieces 820 of dissolvable material. The cross pieces 820 may function in part to strengthen the filter. The cross pieces 820 may also function at least in part to prevent an embolism of the filter. For example, if a portion of the dissolvable material making up the filter dissolves first and begins to break away from the rest of the filter cross pieces 820 may function to retain the dissolving piece with the remainder of the filter. In one embodiment, the cross pieces 820 are made of material that is thicker, i.e. slower dissolving, at the periphery than the material at the center of the filter.

In the filters that are made of dissolvable material, the configuration is chosen based at least in part on a tradeoff between the strength provided by the closeness of the pieces or piece of dissolvable material and the negative effect that this closeness has on the laminar flow in the vessel where it will be deployed. The tradeoff is chosen so that the filter is strong enough to hold a clot in the vessel and not break off but not to dense to significantly decrease the flow in the vessel. It is generally desired not to significantly decrease the blood flow because such a decrease can itself cause clots.

In one embodiment it is desirable to have the piece or pieces of dissolvable material closer in the middle of the filter because it increases the strength of the filter in the middle where the flow is strongest. However, the thickness in the middle would also negate the possibility that the center of the filter would dissolve first, therefore there is a tradeoff.

In one embodiment of a venous filter of the invention, the filter is configured to dissolve in the middle before the outsides of the filter dissolves.

Figure 9:
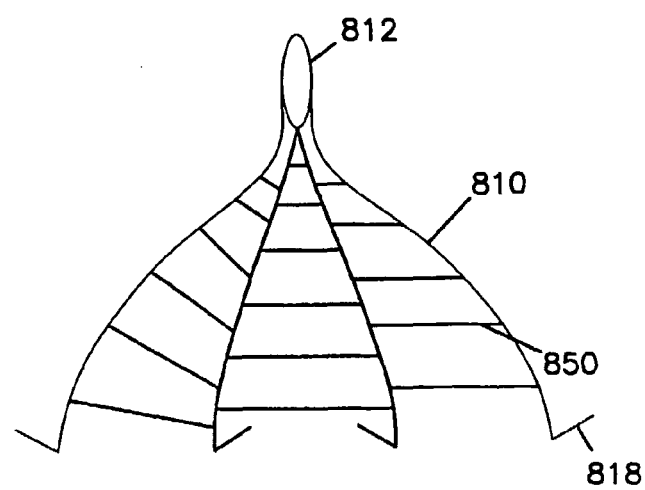
FIG. 9 is a plan view of a venous filter in accordance with the invention.

Another example of a filter that includes some portion that is made of a dissolvable material is seen in FIG. 9. The filter seen in FIG. 9 includes a head 812, struts 810, anchors 818 and lattice pieces 850. In one embodiment, only the lattice pieces 850 are made of a biodegradable material. In another embodiment, the lattice pieces 850, the struts 810 and the head 812 are made of biodegradable material. In such an embodiment, the struts 810 and the head 812 can, but need not be made of material that is stiffer than the lattice pieces 850 to afford the filter a desired level of stiffness.

In an embodiment where the struts 810, the head 812, and the lattice pieces 850 are made of biodegradable material, the lattice pieces 850 are generally made of a material that causes them to degrade before the struts 810 and the head 812. In yet another embodiment where the struts 810, the head 812, and the lattice pieces 850 are made of biodegradable material, the parts that make up the filter are made of materials (either different materials or different configurations of the same material) that causes them to degrade first, followed by the struts 810, and followed by the head 812. Such a configuration would prevent one or more of the struts from being released into the blood stream if the head 812 dissolved first. In the embodiments exemplified above, it is noted that the anchors 818 are not made of biodegradable material. This prevents the filter from being released in full or part by one or more anchors 818 dissolving before some or all of the filter.

Other Features of Some Venous Filters of the Invention

Venous filters of the invention may also include features that are commonly used in known IVC filters. Filters of the invention can also incorporate features such as drug elution, anchoring through a t-tack mechanism, or any combination thereof.

Use of venous filters can sometimes lead to biocompatibility concerns with both the tissue and blood that is in contact with the filter. In some cases, interactions of venous filters with tissue, blood, or some combination thereof can lead to thrombin formation, fibrin formation, intimal hyperplasia, and coagulation cascade, or some combination thereof.

One method of combating complications of biocompatibility issues includes drug elution. Drug elution in the context of devices implanted in a mammalian body, refers to the presentation or release of single or multiple bioactive agents into the blood stream or surrounding tissue by the device or a coating on the device implanted in the mammalian body. The released drug can deposit in and/or effect blood vessels, cells, plaque, or tissues either adjacent to or at a distance from the implanted device, such as a venous filter.

Drugs can be embedded and released from within, "matrix type", or surrounded by and release through "reservoir type" polymer materials that coat ("strut-adherent") or span ("strut-spanning") the struts of the filter. Any combination of these types of configurations may also be utilized in combination with venous filters of the invention. Any single structure, or portion of a structure of the venous filter, or any one or more structures or portions of structures can be coated or impregnated with one or more drugs. In other embodiments, the drug may be linked to the filter surface without the need for a coating by means of detachable bonds that release with time, can be removed by active mechanical or chemical processes, or are in a permanently immobilized form that presents the drug to the flowing blood or surrounding tissue.

Drugs that can be used in drug eluting filters include, but are not limited to antimetabilites such as paclitaxel, and sirolimus; thrombolytic or anti-thrombin III mechanism modifiers such as heparin, hirudin, and tissue factor antibody.

Filters of the invention can also incorporate the use of a T-tack type mechanism for anchoring at least one strut of the venous filter to the wall blood vessel. Examples of such T-tack type mechanisms are commonly used in gastropexy procedures. An example of a specific type of T-tack mechanism includes Brown/Mueller T-fastener available from Meditech/Boston Scientific (Watertown, Mass.). An example of a T-fastener can be found in U.S. Pat. No. 4,705,040, the disclosure of which is incorporated herein by reference.

Figure 10A:
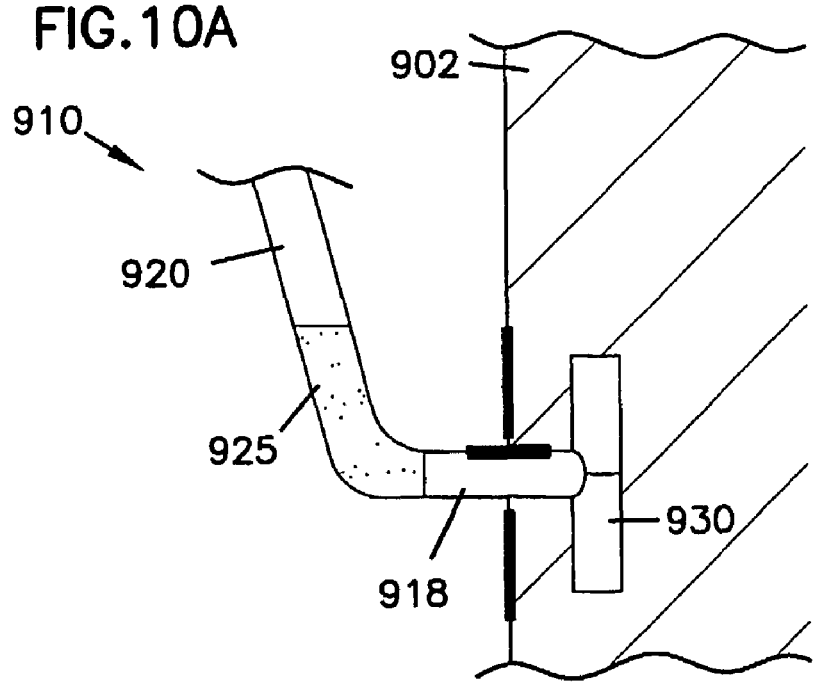
FIGS. 10A and 10B are longitudinal cross sections of a portion of a strut of a filter in accordance with the invention imbedded in a blood vessel wall before (FIG. 10A) and after (FIG. 10B) a temperature change.
Figure 10B:
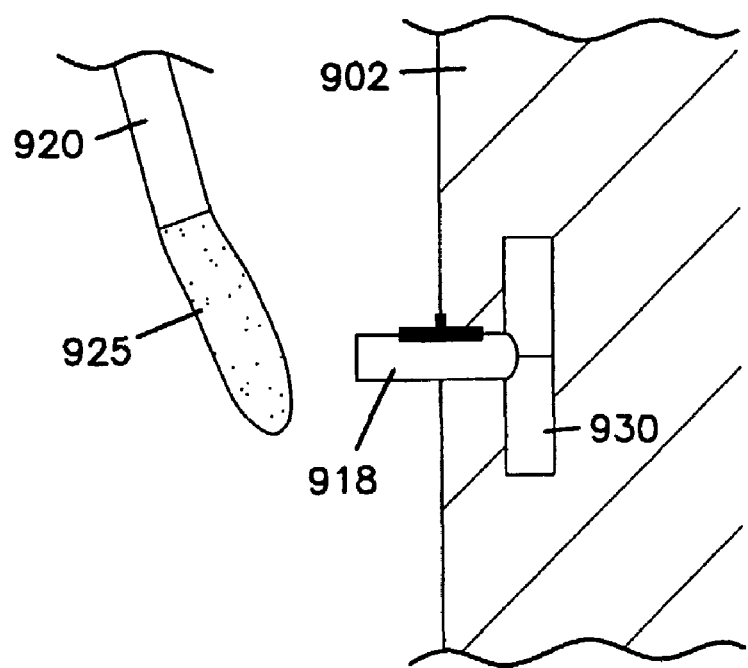

One embodiment of the invention can utilize a T-tack type mechanism in combination with a strut that has a temperature sensitive portion. An example of such an embodiment is depicted in FIG. 10A. In this embodiment, the strut 910 includes a strut portion 920, a temperature sensitive portion 925, and an anchor portion 918. The anchor portion 918 is attached to a T-tack 930, as discussed above. When the temperature around at least the temperature sensitive portion 925 is decreased, the configuration of the temperature sensitive portion 925 changes. FIG. 10B illustrates the configuration of the temperature sensitive portion 925, after the temperature around at least the temperature sensitive portion 925 is decreased. As seen there, the temperature sensitive portion 925, that is weakened by the temperature change, is fractured, leaving the T-tack 930 behind in the wall 904, and allowing the filter to be removed from the blood vessel without damaging the wall of the vessel.

It will also be understood, by one of skill in the art, having read this specification that the venous filters of the invention can be used in combination with any commonly utilized methods of thrombolysis or embolism protection. Examples of such methods include drugs such as, TPA, altaplase, retiplase, recombinant tissue urokinase, streptokinase, and eminase.

The dimensions of filters of the invention are greatly dependent on the ultimate dimensions of the veins in which the filter will be used. Furthermore, the dimensions of the particular portions of the filters, i.e., the temperature sensitive portions and the electrolytically active threads, ardent on the size of the filters. The dimensions of filters and their corresponding pieces would be within one of skill in the art, having read this specification.

Methods of Placing Filters of the Invention

Filters of the invention can generally be placed through any surgical or percutaneous method known to those of skill in the art, for placing commonly used venous filters. Such methods include, but are not limited to, the common femoral vein approach, the Internal Jugular approach, and the axillary vein approach.

Filters of the invention can generally be removed through any surgical method or percutaneous method known to those of skill in the art, for removing commonly used venous filters. Such methods include, but are not limited to, the common femoral vein approach, the Internal Jugular approach, and the axillary vein approach. In one embodiment, a filter of the invention is placed and removed using the same surgical approach.

Particular Veins Where Filters of the Invention Can be Deployed

Commonly, filters are placed in the infrarenal IVC (to prevent possible renal vein thrombosis). Filters may be placed via either the transfemoral (pelvic veins and IVC must be free of thrombus) or the transjugular route, often from the right side in both cases. Suprarenal placement is generally only performed in special cases such as thrombotic occlusion of the infrarenal IVC or renal vein thrombosis as a source of pulmonary emboli. Particularly in young patients, temporary filters may be applied for perioperative protection from pulmonary emboli. Patients are generally carefully and meticulously selected for vena cava filter therapy to achieve the maximum benefits and lowest complication rates from the technique.

In one embodiment, a filter of the invention is deployed in any vein in a mammalian body. In another embodiment, a filter of the invention is deployed in the inferior vena cava (IVC).

Indications Where Filters of the Invention Can be Used

Some indications for IVC filter placement include, but are not limited to: contraindication to anticoagulation and complications of anticoagulation, recurrent pulmonary emboli despite anticoagulation, and chronic pulmonary hypertension and reduced cardiac reserve. Relative indications include, but are not limited to: free floating thrombi in the pelvic veins or IVC, deep venous thrombosis (DVT) and planned orthopedic surgery, surgical therapy for pulmonary embolism, and recurrent septic emboli or pulmonary emboli in cancer patients There are a number of particular classes of patients that could benefit from interior vena cava (IVC) filters. These include, but are not limited to pediatric patients, multi-trauma patients, burn, orthopedic and oncologic patients with pelvic or lower extremities oncologic disease under long-term chemotherapy or pre-surgery therapy. For example, patients who under go surgeries such as hip replacement are at risk for deep venous thrombosis and could benefit from a medium term filter to safeguard against pulmonary embolism during the time when they are most at risk. Likewise, patients with neurological disease, immobilized patients and those with lower extremity phlebitis and/or deep vein thrombosis could also benefit. Patients with a hypercoagulable state that cannot receive anti-coagulation medications for various reasons and need coverage to prevent pulmonary deep venous thrombosis could potentially benefit from a temporary medium term filter during the three to six month time frame required for anticoagulation.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A venous filter comprising
   at least two struts each having a connected end and a non-connected end, wherein each of said struts further comprises a strut portion and an anchor portion, and wherein the strut portion and the anchor portion fit together via a positive and a negative thread, and wherein the thread on either of said strut portion, said anchor portion, or both comprises an electrolytically active thread that erodes quickly; and
   a head, wherein said head connects said connected ends of said struts, wherein said strut portion can be separated from said anchor portion at least in part by the application of an electrical current.

2. The venous filter of claim 1, wherein said electrolytically active threads are on said strut portion.

3. The venous filter of claim 1, wherein said electrolytically active threads are on said anchor portion.

4. The venous filter of claim 1, wherein said electrolytically active thread comprises platinum, rhodium, palladium, rhenium, tungsten, gold, silver, tantalum, stainless steel, nickel, titanium, copper, zinc, benzillium, silicon, tin, aluminum, gallium, or combinations thereof.

5. The venous filter of claim 1, wherein said filter has a shape selected from the group consisting of a web, a spiral, and a conical shape.

6. The venous filter of claim 1, wherein said electrolytically active threads erode in less than about two minutes upon application of a current of 0.01-2 milliamps at about 0.1 to 15 volts.

7. The venous filter of claim 1, wherein said electrolytically active threads erode in less than about one minute upon application of a current of 0.01-2 milliamps at about 0.1 to 15 volts.

8. The venous filter of claim 1, wherein said electrolytically active threads comprise a nickel/titanium alloy, a copper/zinc allow, a nickel/aluminum alloy, or combinations thereof.

9. The venous filter of claim 1, wherein the at least two struts are made of an electrolytically active material, and wherein the at least two struts are covered by insulating material except for the positive thread, the negative thread, or both the positive thread and the negative thread.

10. A venous filter comprising
    at least two struts, each having a connected and a non-connected end, wherein each of said struts comprises a strut portion, a temperature sensitive portion and an anchor portion, wherein said temperature sensitive portion is comprised of a temperature sensitive material different from the anchor portion, and wherein said material is located between said strut portion and said anchor portion and provides for separation of the anchor portion from said temperature sensitive portion upon removal of the venous filter at least in part by changing the temperature around at least said temperature sensitive portion; and
    a head, wherein said head connects said connected ends of said struts.

11. The venous filter of claim 10, wherein said temperature sensitive portion comprises nickel-titanium alloys, copper base alloys, or combinations thereof.

12. The venous filter of claim 11, wherein said temperature sensitive portion comprises nitinol.

13. The venous filter of claim 10, wherein said temperature sensitive portion comprises a shape memory alloy.

14. The venous filter of claim 10, wherein said temperature sensitive portion becomes more flexible as the temperature of said temperature sensitive portion is reduced below a normal body temperature.

15. The venous filter of claim 10, wherein said temperature sensitive portion becomes more flexible as the temperature of said temperature sensitive portion is increased above normal body temperature.

16. The venous filter of claim 10, wherein said temperature sensitive portion is configured to coil when the temperature of said temperature sensitive portion is below a normal body temperature.

17. The venous filter of claim 10, wherein the anchor portion comprises a hook, and wherein the temperature sensitive portion is configured to become disengaged from the hook when the temperature of said temperature sensitive portion is reduced below a normal body temperature.

18. The venous filter of claim 10, wherein the anchor portion is at least partially covered by a sleeve, and wherein the sleeve is made of a material that does not change configuration when exposed to a change in temperature.

* * * * *

UNITED STATES PATENT AND TRADEMARK OFFICE
CERTIFICATE OF CORRECTION

PATENT NO. : 7,867,245 B2  
APPLICATION NO. : 10/588863  
DATED : January 11, 2011  
INVENTOR(S) : Neeman et al.

Page 1 of 1

It is certified that error appears in the above-identified patent and that said Letters Patent is hereby corrected as shown below:

In the Specification:

Column 5, line 30, "about 400-50° C" should read --40°-50° C--.

Signed and Sealed this  
Nineteenth Day of March, 2013

Teresa Stanek Rea  
*Acting Director of the United States Patent and Trademark Office*